(12) United States Patent
Chou

(10) Patent No.: US 6,606,991 B2
(45) Date of Patent: Aug. 19, 2003

(54) ADJUSTABLE OROPHARYNGEAL AIRWAY APPARATUS

(76) Inventor: Hsiu-Chin Chou, 3080 Sorrelwood Dr., San Ramon, CA (US) 94583

( * ) Notice: Subject to any disclaimer, the term of this patent is extended or adjusted under 35 U.S.C. 154(b) by 0 days.

(21) Appl. No.: 10/010,599

(22) Filed: Dec. 6, 2001

(65) Prior Publication Data
US 2002/0040712 A1 Apr. 11, 2002

Related U.S. Application Data

(63) Continuation-in-part of application No. 09/288,440, filed on Apr. 8, 1999, now abandoned.

(51) Int. Cl.[7] .............................................. A61M 16/00
(52) U.S. Cl. .............................. 128/200.26; 128/207.14
(58) Field of Search ...................... 128/207.14, 207.17, 128/207.29, 200.26, 859, 860, 863, 200.15, 206.29, DIG. 26, 912

(56) References Cited

U.S. PATENT DOCUMENTS

| | | | |
|---|---|---|---|
| 3,556,103 A | | 1/1971 | Calhoun |
| 3,930,507 A | | 1/1976 | Berman |
| 4,211,234 A | | 7/1980 | Fisher |
| 4,235,229 A | * | 11/1980 | Ranford et al. ........ 128/207.17 |
| 4,275,724 A | | 6/1981 | Behrstock |
| 4,338,930 A | | 7/1982 | Williams |
| 4,356,821 A | | 11/1982 | Rind |
| 4,365,625 A | | 12/1982 | Rind |
| 4,848,331 A | | 7/1989 | Northway-Meyer |
| 5,251,616 A | | 10/1993 | Desch |
| 5,540,224 A | | 7/1996 | Buret et al. |
| 5,720,275 A | | 2/1998 | Patil et al. |
| 5,740,791 A | | 4/1998 | Aves |
| 5,829,430 A | | 11/1998 | Islava |
| 6,474,332 B2 | * | 11/2002 | Arndt ..................... 128/200.26 |

OTHER PUBLICATIONS

Acta Angesthesiologica Scandinavica 1998: 42: 1128; and Chou H–C, Wu T–L. Large hypopharyngeal tongue: a shared.
anatomic abnormality for difficult mask ventilation, difficult intubation, and abstructive sleep apnea ? Anesthesiology 2001; 94: 936–937.
Chou H–c, Wu T–L. Mandibulohyoid Distance In Difficult Laryngoscopy British Journal of Anaesthesia.
1993: 71: 335–339; Chou H–C, wu T–L. Thyromental Distance Should't We Redefine its Role in the Prediction of Difficult.
Laryngoscopy (Letter). Acta Anaesthesilolgica Scandinavica 1998. 42 : 136–137 : Benumof JL. Prediction of Difficult Intubation (Letter).

* cited by examiner

Primary Examiner—Weilun Lo
Assistant Examiner—Mital Patel
(74) Attorney, Agent, or Firm—Thomas R. Lampe

(57) ABSTRACT

An adjustable oropharyngeal airway apparatus includes a rigid airway portion comprising a mouthpiece and a flexible airway portion frictionally engaging and slidably disposed in the mouthpiece. The overall length of the apparatus can be varied by sliding the flexible portion relative to the mouthpiece.

1 Claim, 7 Drawing Sheets

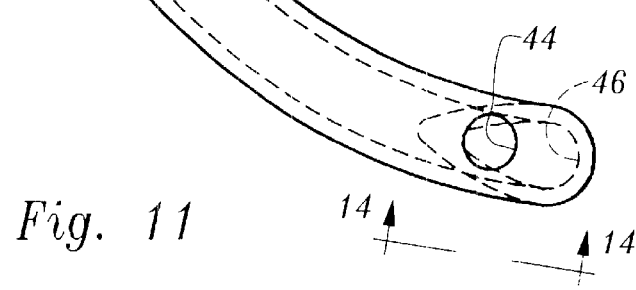
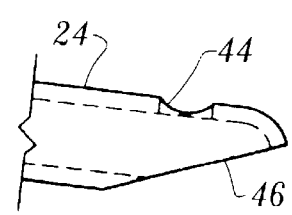

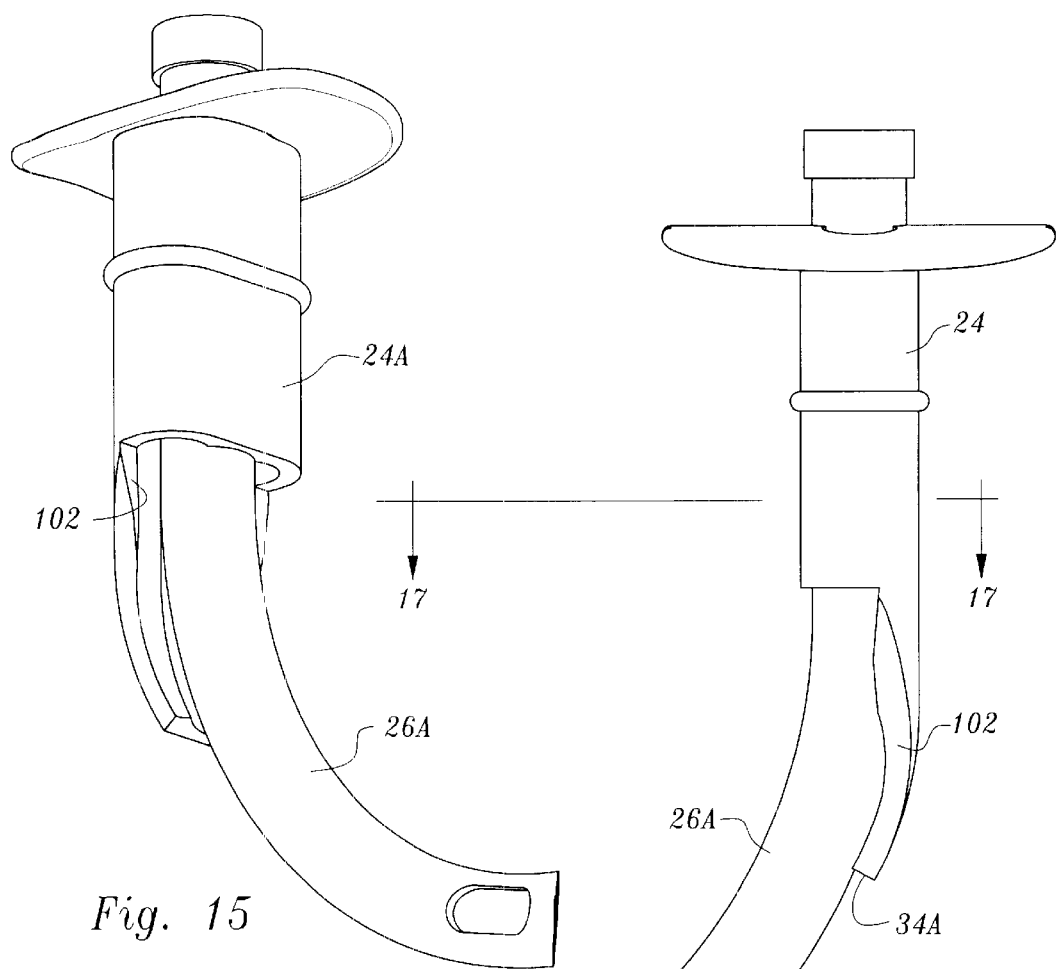
Fig. 15
Fig. 16
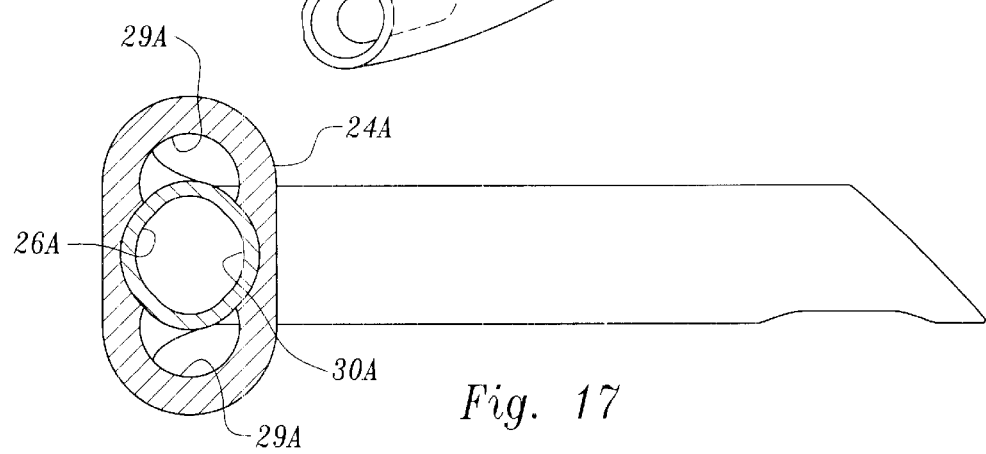
Fig. 17

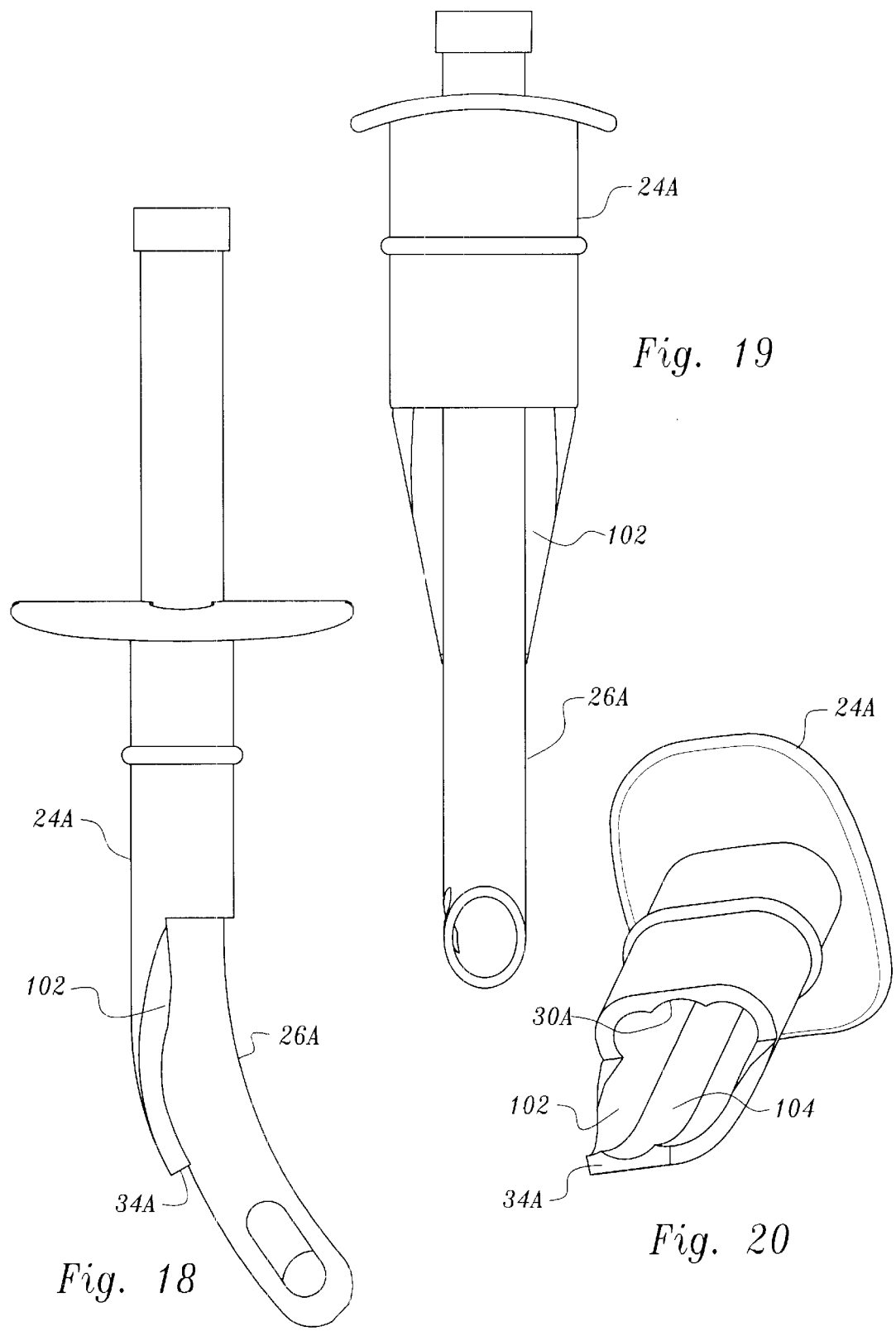

ADJUSTABLE OROPHARYNGEAL AIRWAY APPARATUS

This application is a continuation-in-part of U.S. patent application Ser. No. 09/288,440, filed Apr. 8, 1999 now abandoned.

TECHNICAL FIELD

This invention relates to an oropharyngeal airway employed to maintain an unobstructed air passage in an anesthetized, unconscious or sleeping patient by preventing the patient's tongue from falling backward against the posterior pharyngeal wall and causing the air space to collapse.

BACKGROUND OF THE INVENTION

Commercial prior art oropharyngeal airway devices are conventionally of single-piece construction, being formed, for example, of relatively rigid plastic material. Such construction is for the purpose of preventing the patient from biting down and collapsing the lumen of the oropharyngeal airway. However, the typical rigid oropharyngeal airway is irritating to the patient who is not totally unconscious or who is not in a deep state of general anesthesia.

Furthermore, there are significant numbers of patients in whom the base of the tongue, and hence the larynx, is caudally positioned in the hypopharynx. This condition is discussed in the following publications: Chou H-C, Wu T-L. Mandibulohyoid distance in difficult laryngoscopy *British Journal of Anaesthesia* 1993: 71: 335–339; Chou H-C, Wu T-L. Thyromental distance—shouldn't we redefine its role in the prediction of difficult laryngoscopy (letter). *Acta Anaesthesiologica Scandinavica* 1998: 42: 136–137; Benumof J L. Prediction of difficult intubation (letter). *Acta Anaesthesiologica Scandinavica* 1998: 42: 1128; and Chou H-C, Wu T-L. Large hypopharyngeal tongue: a shared anatomic abnormality for difficult mask ventilation, difficult intubation, and obstructive sleep apnea?. *Anesthesiology* 2001; 94: 936–937. When such condition exists, the commonly available prior art airway devices cannot reach the larynx, the tongue mass cannot be displaced forward and the air passage remains obstructed. Also, the commonly available oropharyngeal airway devices are not easily tolerated in sleeping patients or in patients emerging from general anesthesia when the gag reflex is active while the air passage remains relatively collapsed.

Since the typical commercially available oropharyngeal airway is not made long enough to reach beyond the base of the tongue, as stated above, practitioners often find it necessary to lift the patient's chin up to raise the base of the tongue from the posterior pharyngeal wall in order to maintain an open air passage. Such maneuver ties up the practitioner's hands from performing other essential tasks. This is one of the reasons that anesthesia maintained with a face mask and an oropharyngeal airway is becoming less popular even in connection with a brief surgical procedure. In more severe cases, even jaw lifting with both hands and other maneuvers do not compensate for the deficiencies of commonly available oropharyngeal airways, i.e., the patient cannot be ventilated. If the patient's trachea cannot be intubated immediately, catastrophic results such as hypoxia, brain damage, or even death, can occur.

The adjustable oropharyngeal airway apparatus of the present invention solves the above-described problems. While adjustable airways are known in the prior art they do not incorporate the structural combination and cooperative relationships of the present invention. The following United States patents are considered to be representative of the current state of the prior art in this field: U.S. Pat. No. 3,930,507, issued Jan. 6, 1976, U.S. Pat. No. 5,740,791, issued Apr. 21, 1998, U.S. Pat. No. 4,338,930, issued Jul. 13, 1982, U.S. Pat. No. 4,356,821, issued Nov. 2, 1982, U.S. Pat. No. 4,365,625, issued Dec. 28, 1982, U.S. Pat. No. 5,540,224, issued Jul. 30, 1996, U.S. Pat. No. 4,275,724, issued Jun. 30, 1981, U.S. Pat. No. 3,556,103, issued Jan. 19, 1971, U.S. Pat. No. 5,829,430, issued Nov. 3, 1998, U.S. Pat. No. 5,720,275, issued Feb. 24, 1998, U.S. Pat. No. 5,251,616, issued Oct. 12, 1993, U.S. Pat. No. 4,848,331, issued Jul. 18, 1989, and U.S. Pat. No. 4,211,234, issued Jul. 8, 1980.

As will be seen below, the present invention incorporates a first airway portion in the form of a substantially rigid mouthpiece having an outer mouthpiece surface. The outer mouthpiece surface is engageable by an individual's teeth and the substantially rigid mouthpiece resists deformation caused by biting of the mouthpiece by the individual.

An elongated, tubular second airway portion formed of flexible, substantially soft, yieldable and resilient material is positioned in an interior passageway defined by the mouthpiece. The second airway portion is maintained under compression by the mouthpiece and the second airway portion can be moved relative to the mouthpiece by the application of external forces thereto. The compressive engagement between the mouthpiece and the second airway portion resists relative movement therebetween so that the second airway portion is maintained in any one of a plurality of selected positions after the external forces are removed.

More particularly, the interior passageway of the mouthpiece includes a central passageway section or area receiving the second airway portion and side passageway sections or areas communicating with the central passageway section and disposed on opposed sides thereof which accommodate bulges formed in the second airway portion caused by compression thereof by the mouthpiece and which also provide for the flow of air through the mouthpiece alongside the second airway portion.

There is no teaching or suggestion of the features noted above in the above-identified prior art patents.

U.S. Pat. No. 5,251,616 is of note since it shows an adjustable tracheostomy tube assembly including a flexible tracheostomy tube which is slidably adjustable relative to a rigid neck collar which is located at a surgical opening formed in the patient's neck leading to the trachea. A separate three part locking assembly is affixed to the neck collar and, when tightened into place, lockingly engages the tracheostomy tube about the entire outer periphery of the tracheostomy tube to lock it at a desired position.

The structure of the adjustable tracheostomy tube assembly of U.S. Pat. No. 5,251,616 is completely inappropriate for use as an oropharyngeal airway apparatus and the patent fails to provide any hint or suggestion whatsoever that such might be the case.

Adjustment of the second airway portion relative to the mouthpiece of the invention disclosed herein is quickly and readily accomplished. The second airway portion is maintained at a selected position relative to the mouthpiece without having to manipulate a separate locking means as disclosed in U.S. Pat. No. 5,251,616. Furthermore, in the apparatus disclosed and claimed herein air is allowed to pass through the mouthpiece alongside the second airway portion as well as through the second airway portion, a feature not found in U.S. Pat. No. 5,251,616 and one that is highly desirable in an oropharyngeal airway apparatus.

DISCLOSURE OF INVENTION

The present invention relates to oropharyngeal airway apparatus for positioning in the mouth of an individual and for retention on the individual as a unit to maintain an unobstructed air passageway in the individual extending from the posterior aspect of the individual's tongue past the individual's mouth to the ambient atmosphere.

The adjustable oropharyngeal airway apparatus includes a first airway portion comprising a mouthpiece, the mouthpiece having an outer mouthpiece surface positionable in the mouth of the individual. The mouthpiece includes an inner first airway portion end, an outer first airway portion end, a first airway portion interior passageway extending the length thereof, and openings at the inner and outer first airway portion ends communicating with said first airway portion interior passageway.

The mouthpiece is of unitary, substantially rigid construction for resisting deformation of the mouthpiece when the mouthpiece is placed in the mouth of the individual and the individual's teeth bite the outer mouthpiece surface. The mouthpiece is of a length insufficient for the inner first airway portion end to reach the posterior aspect of the individual's tongue where the gag reflex is active when the mouthpiece is positioned in the mouth of the individual.

The first airway portion interior passageway includes a central passageway section and side passageway sections communicating with the central passageway section and disposed on opposed sides thereof.

The apparatus also includes an elongated, double-ended second airway portion substantially longer than the mouthpiece. The second airway portion has a second airway portion interior and openings at opposed ends thereof communicating with the second airway portion interior. One of the opposed ends is a distal end. The second airway portion is positioned in the mouthpiece interior passageway within the central passageway section and is selectively slidably movable relative to the mouthpiece to vary the distance the distal end of the second airway portion is spaced from the inner first airway portion end.

The distal end of the second airway portion is positionable in the individual and projects from the inner first airway portion end, slidable movement of the second airway portion relative to the mouthpiece changing the distance between said distal end and the mouthpiece. The second airway portion is of sufficient length that slidable movement of the second airway portion relative to the mouthpiece enables the distal end to reach or pass the posterior aspect of the individual's tongue when the second airway portion is slid relative to the mouthpiece to position the distal end a selected distance from said inner first airway portion end.

The second airway portion is tubular and formed of flexible, substantially soft, yieldable, resilient material at its distal end and along the length thereof to lessen the likelihood of gagging reflex in the individual and discomfort to the individual. The second airway portion frictionally engages the mouthpiece at the central passageway section and is maintained under compression by the mouthpiece at all times.

Frictional engagement between the second airway portion and the mouthpiece at the central passageway section and compression of the second airway portion by the mouthpiece at the central passageway section resists relative sliding movement therebetween whereby the length of the second airway portion between the distal end and the inner first airway portion end may be adjusted while in the individual's mouth by applying manual force to the second airway portion.

The selected adjusted length of the second airway portion between the distal end and the inner first airway portion end is solely maintained by the frictional engagement between the mouthpiece and the second airway portion at the central passageway section and compression of the second airway portion by the mouthpiece in the absence of application of the manual force. The side passageway sections accommodate bulges formed in the second airway portion during compression thereof by the mouthpiece and provide for flow of air through the mouthpiece alongside the second airway portion.

The apparatus further includes means for limiting relative movement between the mouthpiece and the second airway portion to limit the distance between the distal end of the second airway portion and the inner first airway portion end.

Other features, advantages and objects of the present invention will become apparent with reference to the following description and accompanying drawings.

BRIEF DESCRIPTION OF DRAWINGS

FIG. 11 is a side, elevational view of the flexible second airway portion of the apparatus;

FIG. 12 is an enlarged, cross-sectional view taken along the line 12—12 of FIG. 11;

FIG. 13 is an enlarged, cross-sectional view taken along the line 13—13 of FIG. 11;

FIG. 14 is a bottom view of the distal end of the flexible airway portion as delineated by line 14—14 in FIG. 11;

FIG. 15 is a perspective view of an alternative embodiment of the invention;

FIG. 16 is a side, elevational view of the alternative embodiment;

FIG. 17 is an enlarged cross-sectional view taken along the line 17—17 in FIG. 16;

FIG. 18 is a side, elevational view of the alternative embodiment showing the mouthpiece and second airway portion thereof in relative positions differing from what is shown in FIG. 16;

FIG. 19 is a front, elevational view of the alternative embodiment; and

FIG. 20 is a perspective view of the mouthpiece of the alternative embodiment.

MODES FOR CARRYING OUT THE INVENTION

Figure 2:
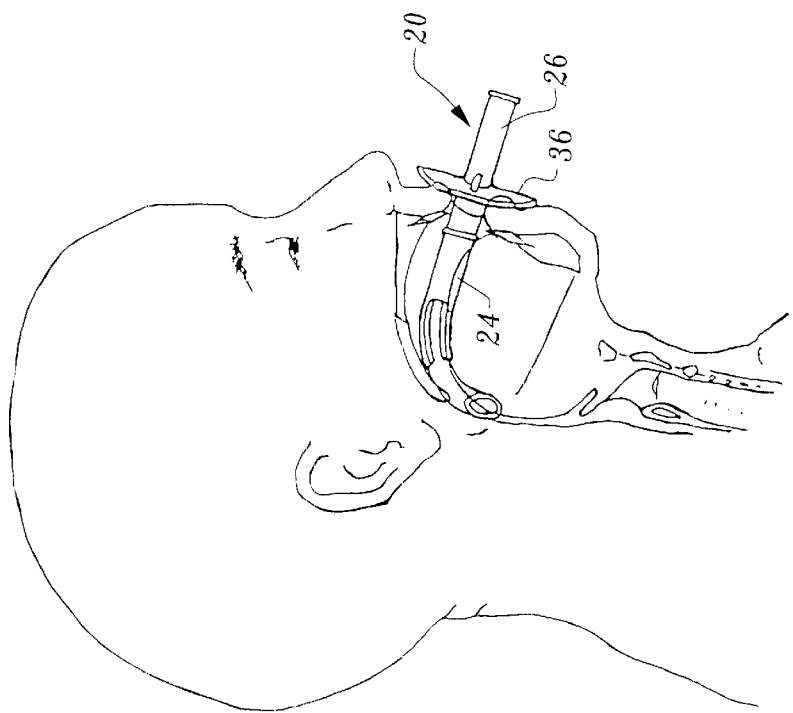
FIG. 2 is a view similar to FIG. 1, but illustrating an airway apparatus constructed in accordance with the teachings of the present invention in place, with the flexible portion of the apparatus not extended to the full operational length thereof.
Figure 1:
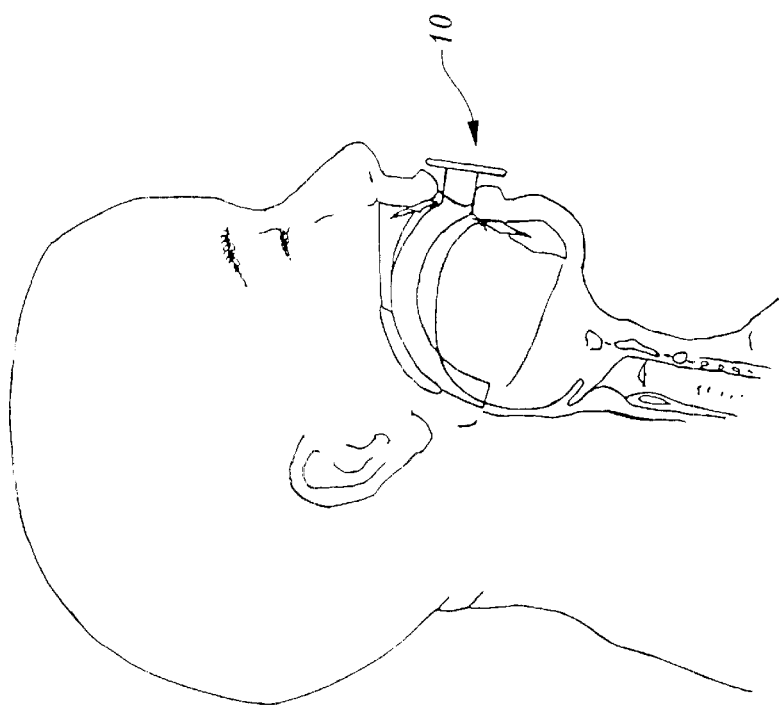
FIG. 1 is an elevational view illustrating a conventional prior art airway in the mouth of a patient having an excessive hypopharyngeal tongue mass, the air passage to the glottis remaining obstructed.
Figure 4:
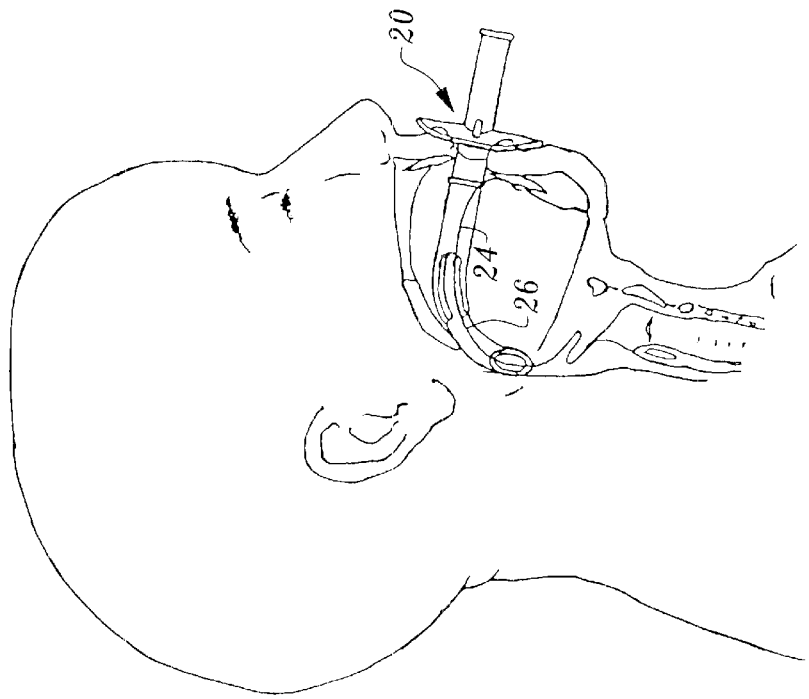
FIG. 4 is a view similar to FIG. 2 illustrating a patient with normal anatomy without excessive hypopharyngeal tongue mass and the flexible portion of the apparatus not fully extended.

Referring now to FIG. 1, an airway 10 of typical and conventional prior art construction is illustrated. The airway is located in a patient with an excessive hypopharyngeal tongue mass. It will be seen that even with the prior art airway 10 in place, the air passage to the glottis remains obstructed.

Referring now to FIGS. 2–14, adjustable oropharyngeal apparatus constructed in accordance with the teachings of the present invention is illustrated, such apparatus being generally designated by reference numeral 20. Airway apparatus 20 includes two airway portions—a first airway portion comprising a rigid mouthpiece 24 formed of molded plastic or the like and a flexible second airway portion 26 which may also be formed of plastic material but a plastic material that is flexible, soft, yieldable and resilient. A suitable rigid portion material is polyethylene and a suitable material employed in the construction of flexible portion 26 is polyvinyl chloride; however, it is to be understood that other suitable materials having the indicated characteristics may be utilized.

The two components or airway portions 24, 26 are formed separately and subsequently assembled together for use as a unit.

Mouthpiece 24 has an interior passageway 28 with a central rounded section or area 30. The rounded section 30 slidably receives therein the tubular-shaped flexible portion 26. The diameter of central section 30 is less than the outer diameter of flexible portion 26 so that compressive forces are exerted on the flexible portion 26 by the mouthpiece 24 at the location of central section 30 and frictional engagement between the rigid and flexible airway portions will prevent relative movement therebetween in the absence of outside forces of sufficient magnitude to cause relative movement being applied thereto.

The interior passageway 28 also includes side passageway sections or areas 29 (See FIGS. 8 and 9) communicating with central rounded passageway section 30. These side passageway sections or areas are disposed on opposed sides of central section 30 and accommodate bulges formed in the flexible airway portion 26 caused by compression thereof. In addition, the side passageway sections 29 allow flow of air through the mouthpiece alongside airway portion 26. Breathing through the mouth can still take place (in the absence of a total obstruction in the patient) even when the flexible airway portion becomes temporarily obstructed. Ventilation of the patient can be carried out during manipulation of the flexible airway portion.

Mouthpiece 24 not only serves as a conduit for the flexible portion, it also protects the flexible portion from the biting force of the patient's teeth applied to the outside surface of the mouthpiece. The rigid mouthpiece is significantly shorter than typical or common oropharyngeal airways so that it will not reach the posterior aspect of the tongue where the gag reflex is active. This location of course varies between patients.

Figure 7:
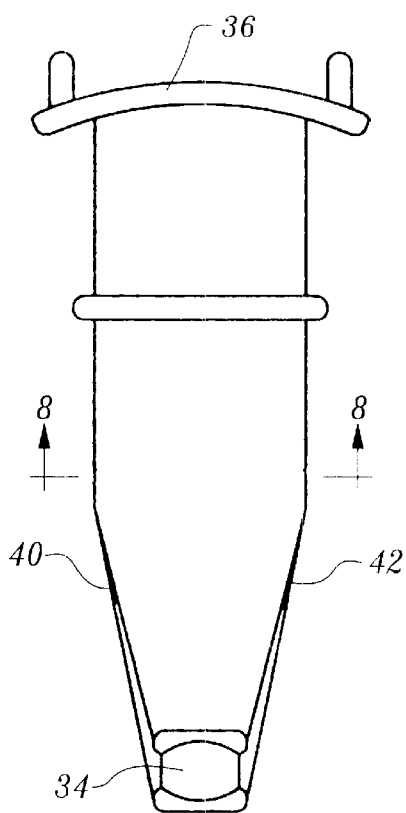
FIG. 7 is a frontal, elevational view of the rigid first airway portion of the apparatus.
Figure 9:
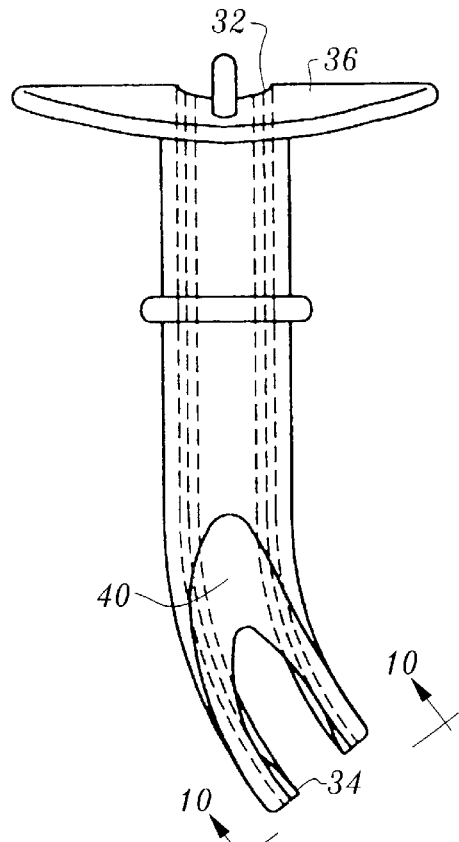
FIG. 9 is a side, elevational view of the rigid first airway portion.
Figure 8:
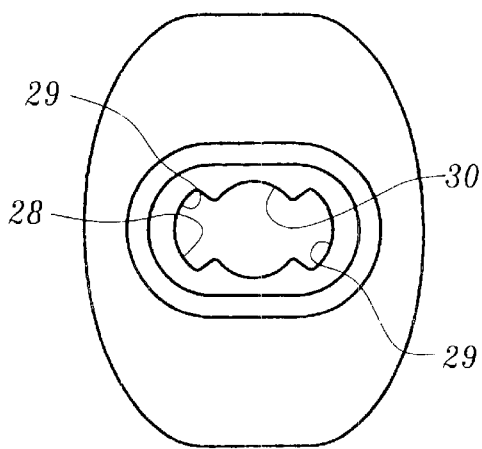
FIG. 8 is a cross-sectional view taken along the line 8—8 in FIG. 7.
Figure 10:
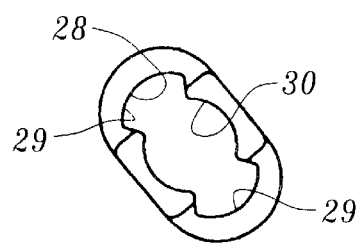
FIG. 10 is a view of the rigid first airway portion as taken along the line 10—10 in FIG. 9.

The rigid first airway portion or mouthpiece 24 has spaced open ends, an outer first airway portion end 32 and an inner first airway portion end 34. A curved plate 36 is located at the outer end 32 and is engageable with the outer mouth area of the patient to properly position the mouthpiece relative to the patient when in use. With particular reference to FIGS. 7 and 9, the mouthpiece has opposed, tapered sides 40, 42 adjacent to the inner first airway portion end defining side openings communicating with the opening at inner first airway portion end 34. This reduces bulk of the apparatus at the inner end of the mouthpiece to minimize patient discomfort.

Figure 3:
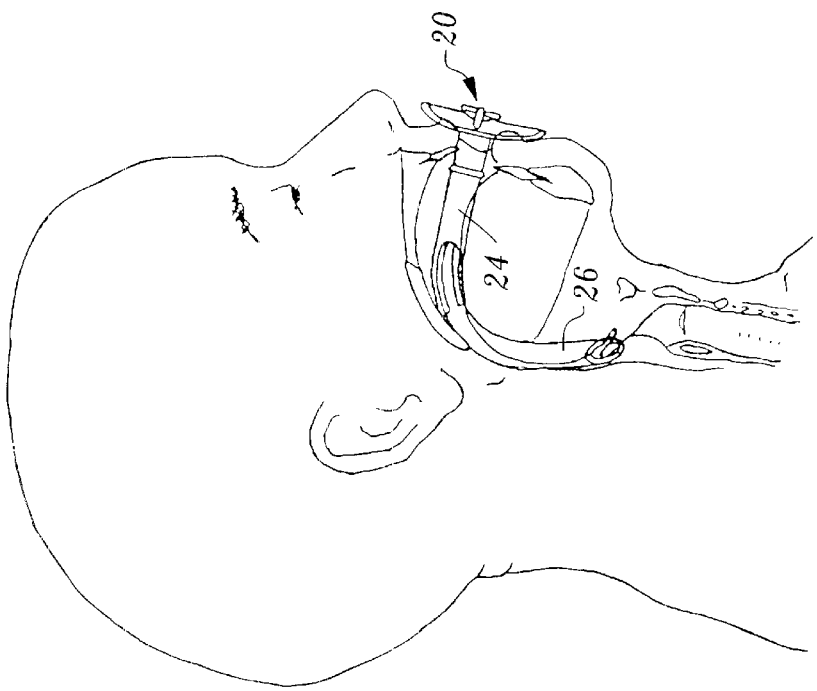
FIG. 3 is a view similar to FIG. 2, but illustrating the flexible portion extended to maintain an unobstructed air passage from the mouth-piece of the apparatus all the way down to the patient's glottis.
Figures 5, 6:
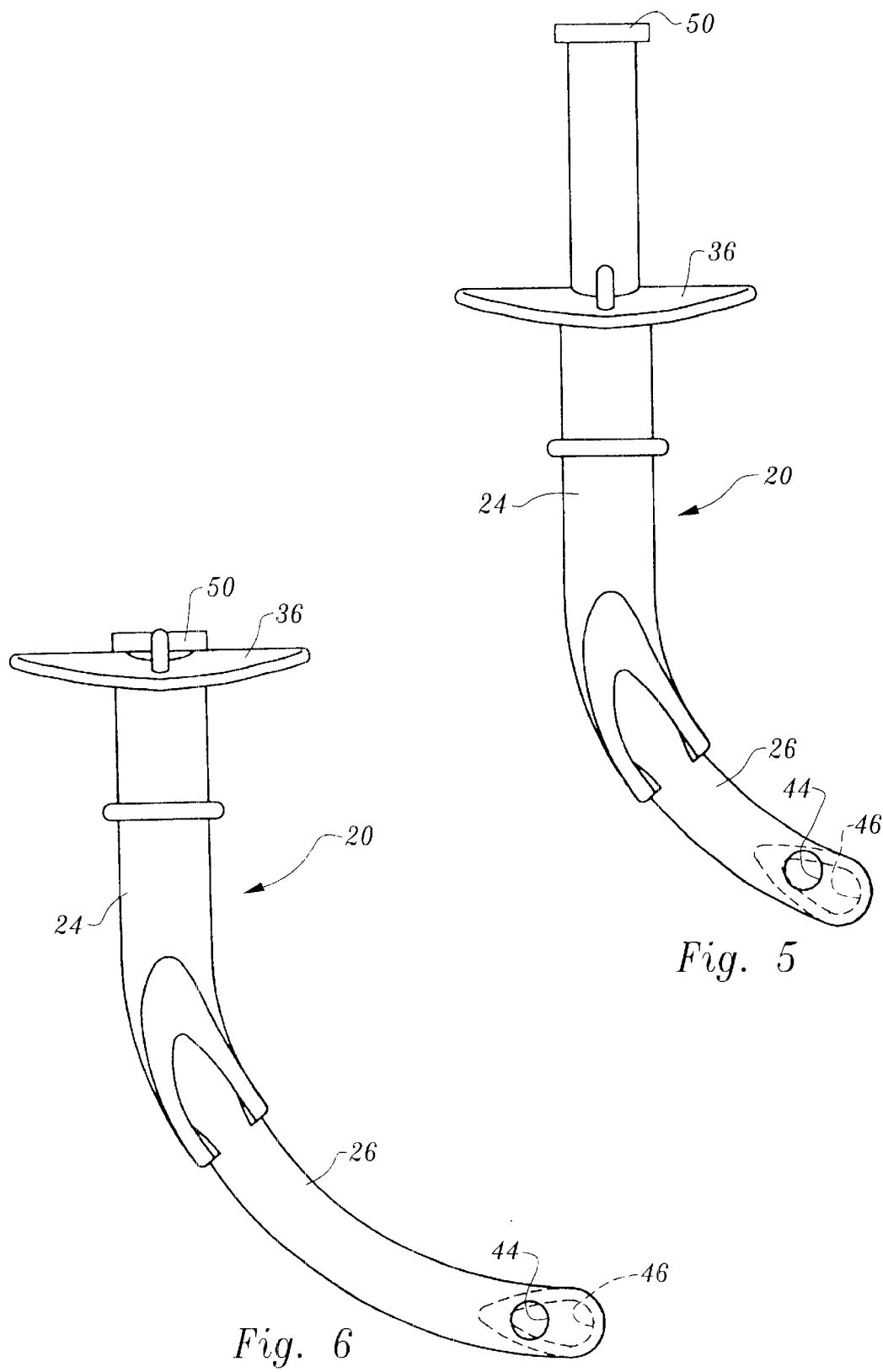
FIG. 5 is an elevational view of apparatus constructed in accordance with the teachings of the present invention showing the flexible portion of the apparatus in partially extended position.
FIG. 6 is a view similar to FIG. 5, but illustrating the flexible portion fully extended.

The flexible portion 26 is considerably longer than conventional oropharyngeal airways. The flexible portion is capable of reaching the base of the tongue to provide a patent or unobstructed air passageway even in patients with a very caudally positioned larynx and large hypopharyngeal tongue mass, as illustrated in FIG. 3.

The relative softness of the flexible portion allows it to conform to the patient's anatomy. The flexible airway portion glides over the patient's tongue mass and creates an air passageway between the tongue mass and the posterior pharyngeal wall. It is less irritating to the pharyngeal tissue than rigid materials and thus is less likely to cause gagging reflex or discomfort to the patient. The patient can tolerate the presence of the airway apparatus of the present invention better than conventional arrangements. Thus, it is possible to use this improved airway in semi-awake patients during emergence from general anesthesia or in semi-conscious patients in emergency resuscitation situations to provide an adequate air passage for ventilation.

The intra-oral length of the flexible portion can be adjusted while the oropharyngeal airway apparatus of the present invention is in a patient's mouth. By moving the flexible portion up or down while ventilating the patient through a face mask, one can find the optimal airway length for the patient to maximize air passage easily and instantaneously, without taking the oropharyngeal airway apparatus out of the mouth and trying another size of the airway. Because of the adjustability feature, although the apparatus of the present invention can be made in several sizes, the required number of available sizes can be significantly reduced as compared to prior art airways. The apparatus provides a savings both as to cost and time and provides better airway management for practitioners in both normal and difficult clinical situations.

The lower or distal end segment of the flexible airway portion 26 is tapered as shown in FIG. 14 and two openings 44, 46 are located at opposed sides of the distal end and spaced from one another. This will allow air flow even if one of the openings is blocked by tissue. The taper of the distal end also contributes to the ease of advancing the flexible portion within the patient's mouth.

Downward sliding movement of the flexible airway portion 26 relative to the mouthpiece 24 is limited by a projecting member 50 disposed around opening 52 at the upper or outer end of flexible portion 26. That is, projecting member 50 will engage plate 36 on the rigid airway portion to prevent further downward movement of the flexible airway portion.

An alternative embodiment of the invention is shown in FIGS. 15–20. In this embodiment a portion of the mouthpiece 24A adjacent to the inner end 34A forms a recess 102. This configuration lessens the chance that the mouthpiece will irritate the patient's tongue. The adjacent tubular portion of the mouthpiece forms central rounded passageway section 30A and side passageway sections 29A. FIG. 17 shows bulges formed in flexible portion 26A due to compression of the flexible portion by the mouthpiece accommodated by the side passageway sections. A curved channel 104 leads from one side of central rounded passageway section to act as a guide for the flexible portion 29A.

The invention claimed is:

1. Adjustable oropharyngeal airway apparatus for positioning in the mouth of an individual and for retention in the individual's mouth as a unit to maintain an unobstructed air passageway in the individual extending from the posterior aspect of the individual's tongue past the individual's mouth to the ambient atmosphere, said adjustable oropharyngeal airway apparatus comprising, in combination:

a first airway portion comprising a mouthpiece, said mouthpiece having an outer mouthpiece surface positionable in the mouth of the individual having an inner first airway portion end, an outer first airway portion end, a first airway portion interior passageway extending the length thereof, and openings at the inner and outer first airway portion ends communicating with said first airway portion interior passageway, said mouthpiece being of unitary, substantially rigid construction for substantially resisting deformation of said mouthpiece when the mouthpiece is placed in the mouth of the individual and the individual's teeth bite said outer mouthpiece surface, said mouthpiece further including mouth engaging structure located at said outer end extending outwardly from said outer mouthpiece surface and engageable with the outer mouth area of the individual to position the mouthpiece at a predetermined position relative to the individual, and said mouthpiece being of a length insufficient for the inner first airway portion end to reach the posterior aspect of the individual's tongue where the gag reflex is active when said mouthpiece is positioned in the mouth of the individual when said mouth engaging structure engages the outer mouth area of the individual, the first airway portion interior passageway including a central passageway section and at least one side passageway section communicating with said central passageway section and disposed on a side thereof;

an elongated, double-ended second airway portion substantially longer than said mouthpiece having a second airway portion interior and openings at opposed ends thereof communicating with said second airway portion interior, one of the opposed ends thereof being a distal end, said second airway portion having a substantially smooth second airway portion exterior surface positioned in said mouthpiece interior passageway within the central passageway section and selectively slidably movable relative to said mouthpiece while in continuous contact with the central passageway section to vary the distance the distal end of said second airway portion is spaced from the inner first airway portion end, the distal end of said second airway portion positionable in the individual and projecting from the inner first airway portion end, slidable movement of said second airway portion relative to the mouthpiece while the substantially smooth second airway portion exterior surface is in continuous contact with the central passageway section changing the distance between said distal end and said mouthpiece and said second airway portion being of sufficient length that slidable movement of said second airway portion relative to said mouthpiece while in continuous engagement therewith enables said distal end to reach or pass the posterior aspect of the individual's tongue when said second airway portion is slid relative to said mouthpiece to position the distal end a selected distance from said inner first airway portion end, said second airway portion being tubular and formed of flexible, substantially soft, yieldable, resilient material at said distal end and along the length thereof to lessen the likelihood of gagging reflex in the individual and discomfort to the individual, said second airway portion being maintained under compression by said mouthpiece at said central passageway section at all times, and continuous frictional engagement between said second airway portion and said mouthpiece at said central passageway section and compression of said second airway portion by said mouthpiece at said central passageway section continuously resisting relative sliding movement therebetween whereby the length of the second airway portion between said distal end and the inner first airway portion end may be adjusted while in the individual's mouth by applying manual force to the second airway portion, and the selected adjusted length of the second airway portion between said distal end and the inner first airway portion end being solely maintained by the frictional engagement between said mouthpiece and said second airway portion at said central passageway section and compression of said second airway portion by said mouthpiece in the absence of application of said manual force, said at least one side passageway section accommodating a bulge formed in said second airway portion during compression thereof by the mouthpiece spaced from said mouthpiece whereby said at least one side passageway provides for flow of air through the mouthpiece alongside the second airway portion; and means for limiting relative movement between said mouthpiece and said second airway portion to limit the distance between the distal end of the second airway portion and said inner first airway portion end, said means for limiting relative movement including a projecting member projecting outwardly from said second airway portion for abutting against said mouth engaging structure during slidable movement of said second airway portion relative to said mouthpiece, said mouthpiece defining a recess adjacent to the inner first airway portion end, said mouthpiece additionally defining a curved channel for guiding said second airway portion leading from said central passageway section to the inner first airway portion end and away therefrom in a direction allowing passage of the second airway portion alongside and past the tongue of the individual between the tongue and posterior pharyngeal wall of the individual.

* * * * *